(12) United States Patent
Dahlen et al.

(10) Patent No.: US 10,959,636 B2
(45) Date of Patent: Mar. 30, 2021

(54) CATHETER WITH HIGH-DENSITY MAPPING ELECTRODES

(71) Applicant: St. Jude Medical, Cardiology Division, Inc., St. Paul, MN (US)

(72) Inventors: Travis Dahlen, Forest Lake, MN (US); Rishi Manda, Stillwater, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 16/800,156

(22) Filed: Feb. 25, 2020

(65) Prior Publication Data

US 2020/0245887 A1 Aug. 6, 2020

Related U.S. Application Data

(62) Division of application No. 16/150,429, filed on Oct. 3, 2018, now Pat. No. 10,702,178.

(60) Provisional application No. 62/572,186, filed on Oct. 13, 2017.

(51) Int. Cl.
*A61B 5/042* (2006.01)
*A61B 5/00* (2006.01)
*A61B 18/14* (2006.01)
*A61B 18/00* (2006.01)
*A61N 1/362* (2006.01)

(52) U.S. Cl.
CPC .......... *A61B 5/0422* (2013.01); *A61B 5/6858* (2013.01); *A61B 5/6859* (2013.01); *A61B 5/6869* (2013.01); *A61B 18/1492* (2013.01); *A61B 2018/0016* (2013.01); *A61B 2018/00267* (2013.01); *A61B 2018/00351* (2013.01); *A61B 2018/00357* (2013.01); *A61B 2018/00577* (2013.01); *A61B 2018/00839* (2013.01); *A61B 2217/007* (2013.01); *A61B 2218/002* (2013.01); *A61B 2562/221* (2013.01); *A61N 1/362* (2013.01)

(58) Field of Classification Search
CPC .................................... A61B 5/0422
See application file for complete search history.

(56) References Cited

U.S. PATENT DOCUMENTS

| | | | |
|---|---|---|---|
| 4,522,212 | A | 6/1985 | Gelinas et al. |
| 5,702,438 | A | 12/1997 | Avitall |
| 5,964,757 | A | 10/1999 | Ponzi |
| 6,029,091 | A | 2/2000 | de la Rama et al. |
| 6,071,282 | A | 6/2000 | Fleischman |
| 6,123,699 | A | 9/2000 | Webster, Jr. |

(Continued)

FOREIGN PATENT DOCUMENTS

| | | |
|---|---|---|
| AU | 2015202258 B2 | 6/2016 |
| EP | 2664295 A1 | 11/2013 |

(Continued)

*Primary Examiner* — Lee S Cohen
(74) *Attorney, Agent, or Firm* — Dykema Gossett PLLC

(57) ABSTRACT

High-density mapping catheters with an array of mapping electrodes are disclosed. These catheters can be used for diagnosing and treating cardiac arrhythmias, for example. The catheters are adapted to contact tissue and comprise a flexible framework including the electrode array. The array of electrodes may be formed from a plurality of columns of longitudinally-aligned and rows of laterally-aligned electrodes.

12 Claims, 11 Drawing Sheets

(56) References Cited

U.S. PATENT DOCUMENTS

| | | |
|---|---|---|
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,415,187 B1 | 7/2002 | Kuzma et al. |
| 6,522,932 B1 | 2/2003 | Kuzma et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,228,164 B2 | 6/2007 | Fuimaono et al. |
| 7,257,435 B2 | 8/2007 | Plaza |
| 7,412,274 B2 | 8/2008 | Mejia |
| 7,429,261 B2 | 9/2008 | Kunis et al. |
| 7,561,907 B2 | 7/2009 | Fuimaono et al. |
| 8,271,099 B1 | 8/2012 | Swanson |
| 8,391,947 B2 | 3/2013 | Urman et al. |
| 8,486,063 B2 | 7/2013 | Werneth et al. |
| 8,565,894 B2 | 10/2013 | Vetter et al. |
| 8,603,069 B2 | 12/2013 | Selkie |
| 8,744,599 B2 | 6/2014 | Tegg |
| 9,044,245 B2 | 6/2015 | Condie et al. |
| 9,820,664 B2 | 11/2017 | Hoitink et al. |
| 9,907,480 B2 | 3/2018 | Basu et al. |
| 9,949,656 B2 | 4/2018 | Wu et al. |
| 10,194,994 B2 | 2/2019 | Deno et al. |
| 10,285,610 B2 | 5/2019 | Wu |
| 10,578,737 B2 | 3/2020 | Gliner et al. |
| 10,702,177 B2 | 7/2020 | Aujla |
| 2005/0159741 A1 | 7/2005 | Paul et al. |
| 2009/0198300 A1 | 8/2009 | Zhang et al. |
| 2011/0118726 A1 | 5/2011 | de la Rama et al. |
| 2012/0271138 A1 | 10/2012 | Kordis et al. |
| 2012/0271139 A1 | 10/2012 | Kordis et al. |
| 2012/0271302 A1 | 10/2012 | Behl et al. |
| 2012/0296232 A1 | 11/2012 | Ng |
| 2013/0253504 A1 | 9/2013 | Fang |
| 2013/0274582 A1 | 10/2013 | Afonso et al. |
| 2014/0200639 A1 | 7/2014 | de la Rama |
| 2014/0288552 A1 | 9/2014 | Kunis et al. |
| 2014/0296902 A1 | 10/2014 | Huszar et al. |
| 2014/0316496 A1 | 10/2014 | Masson et al. |
| 2014/0350564 A1 | 11/2014 | Huszar et al. |
| 2015/0105645 A1 | 4/2015 | Subramaniam et al. |
| 2015/0141785 A1 | 5/2015 | Hayam et al. |
| 2015/0159741 A1 | 6/2015 | Versteyhe et al. |
| 2015/0208937 A1 | 7/2015 | Bullinga |
| 2015/0282859 A1 | 10/2015 | Bencini et al. |
| 2015/0351652 A1 | 12/2015 | Marecki et al. |
| 2016/0143588 A1 | 5/2016 | Hoitink et al. |
| 2016/0213916 A1 | 7/2016 | de la Rama |
| 2016/0317094 A1 | 11/2016 | Byrd et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 * | 2/2017 | Deno ............... A61B 5/062 |
| 2017/0112404 A1 | 4/2017 | de la Rama et al. |
| 2017/0112405 A1 | 4/2017 | Sterrett et al. |
| 2017/0319269 A1 | 11/2017 | Oliverius et al. |
| 2017/0367756 A1 | 12/2017 | Sliwa et al. |
| 2018/0050190 A1 | 2/2018 | Masson |
| 2018/0070845 A1 | 3/2018 | Hoitink et al. |
| 2018/0116539 A1 | 5/2018 | Olson et al. |
| 2018/0193089 A1 | 7/2018 | Wu |
| 2018/0296111 A1 | 10/2018 | Deno |
| 2019/0015007 A1 | 1/2019 | Rottmann |

FOREIGN PATENT DOCUMENTS

| | | |
|---|---|---|
| EP | 2732843 B1 | 5/2014 |
| EP | 2752153 A1 | 7/2014 |
| EP | 2907462 B1 | 9/2018 |
| WO | 2014113612 A1 | 7/2014 |
| WO | 2016001015 A1 | 1/2016 |
| WO | 2017070531 A1 | 4/2017 |

* cited by examiner

C-C

D-D

C-C

C-C

D-D

B-B

B-B

B-B

CATHETER WITH HIGH-DENSITY MAPPING ELECTRODES

CROSS-REFERENCE TO RELATED APPLICATIONS

This application is a divisional of U.S. application Ser. No. 16/150,429, filed 3 Oct. 2018, now U.S. Pat. No. 10,702,178, issued 7 Jul. 2020, which claims the benefit of U.S. Provisional Application No. 62/572,186, filed 13 Oct. 2017.

BACKGROUND a. Field

The instant disclosure relates to high-density electrophysiology mapping catheter assemblies and to map-ablate catheter assemblies for diagnosing and treating cardiac arrhythmias via, for example, radiofrequency ablation. In particular, the instant disclosure relates to flexible high-density mapping catheter assemblies, and to flexible ablation catheter assemblies including onboard, high-density mapping electrodes.

b. Background Art

Intravascular catheters have been used for non-invasive cardiac medical procedures for many years. Catheters may be used, for example, to diagnose and treat cardiac arrhythmias, while positioned within a patient's vasculature that is otherwise inaccessible without a more invasive procedure.

Conventional electrophysiology mapping catheters may include, for example, a plurality of adjacent ring electrodes encircling a longitudinal axis of the catheter and constructed from platinum or some other metal. These ring electrodes may be relatively rigid. Similarly, conventional ablation catheters may comprise a relatively rigid tip electrode for delivering therapy (e.g., delivering RF ablation energy) and may also include a plurality of adjacent ring electrodes. In many applications, it can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If contact between the electrodes and tissue cannot be sufficiently maintained, quality lesions or accurate mapping are unlikely to result.

The foregoing discussion is intended only to illustrate the present field and should not be taken as a disavowal of claim scope.

BRIEF SUMMARY

The instant disclosure relates to high-density electrophysiology mapping catheter assemblies and to map-ablate catheter assemblies for diagnosing and treating cardiac arrhythmias via, for example, radio-frequency ablation. In particular, the instant disclosure relates to flexible high-density mapping catheter assemblies, and to flexible ablation catheter assemblies including onboard high-density mapping electrodes.

Aspects of the present disclosure are directed to basket catheters including an elongated catheter shaft with proximal and distal ends, a flexible basket catheter with a plurality of splines, and a plurality of electrodes mounted to the splines. The flexible basket catheter is coupled to the distal end of the catheter shaft and conforms to tissue when extended into a deployed configuration. The plurality of electrodes are further organized into triangular-shaped cliques along each of the splines. In more specific embodiments, each of the splines nest with adjacent splines when the flexible basket catheter is actuated into a contracted configuration.

Some embodiments are directed to a planar array catheter including an elongated catheter shaft with proximal and distal ends. The elongated catheter shaft defines a catheter longitudinal axis extending between the proximal and distal ends. The planar array catheter further includes a flexible, planar array coupled to the distal end of the catheter shaft. The planar array conforms to tissue, and includes two or more arms extending substantially parallel with the longitudinal axis. Each of the arms has a plurality of electrodes mounted thereon. The electrodes on each arm are grouped into cliques of three or more electrodes defining a two-dimensional shape. In some specific embodiments, the plurality of electrodes on each arm are situated in at least two columns oriented substantially parallel with the longitudinal axis.

Various embodiments of the present disclosure are directed to a linear catheter including an elongated catheter shaft with proximal and distal ends, and a flexible, distal tip assembly at the distal end of the catheter shaft. The distal tip assembly conforms to tissue, and includes a plurality of electrodes. The plurality of electrodes are grouped into cliques of three or more electrodes, with each clique sampling the electrical characteristics of contacted tissue in at least two substantially transverse directions. In such embodiments, the center-to-center distance between the electrodes in each clique may be between 0.5 and 4 millimeters. In various specific embodiments, the electrical characteristics sampled by the electrodes in the clique are collectively indicative of the true electrical characteristics of the contacted tissue independent of the orientation of the linear catheter relative to the tissue.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which.

Figure 1A:
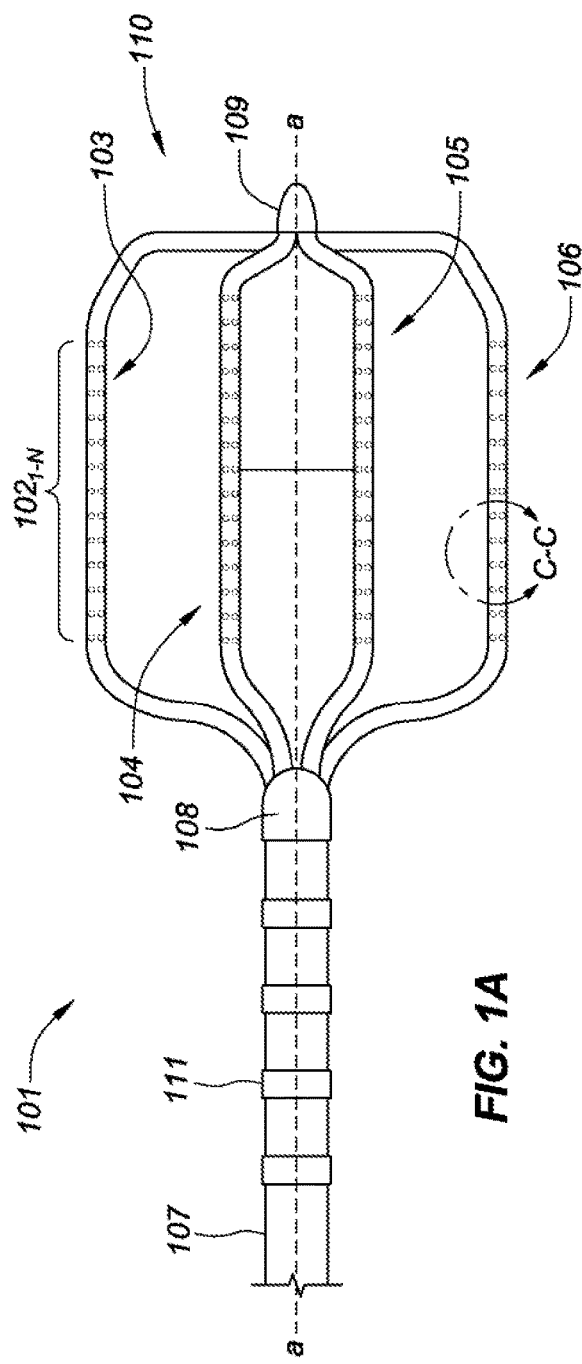
FIG. 1A a plan view of a tip portion of a planar array catheter for high-density electrophysiology mapping, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Various embodiments of the present disclosure are directed to flexible, high-density electrophysiology mapping catheters and map-ablate catheters. In general, the distal portions of these various catheters may comprise an underlying support framework that is adapted to conform to and remain in contact with tissue (e.g., a beating heart wall).

Aspects of the present disclosure are directed toward planar array catheters and basket catheters for electrophysiology mapping. More specifically, many embodiments of the present disclosure utilize printed circuit boards (e.g., flexible printed circuit boards) to form the planar array arms and/or basket splines. Further, aspects of the present disclosure include a plurality of electrodes positioned along the planar array arms and/or basket splines. In such embodiments, the planar array arms and/or basket splines may have electrodes conductively coupled to the flexible circuit boards that at least partially form arms and/or splines. Resulting cliques (or groups) of independently addressable electrodes facilitate electrophysiology measurements of tissue, in contact with the electrodes, which are orientation independent. That is, measurements may be taken across bi-pole pairs of electrodes within each clique (with a known distance therebetween) to capture measurements in at least two orthogonal orientations. In more advanced three-dimensional electrogram analysis, electrophysiology measurements may be captured in three orthogonal planes. In some embodiments, it may be desirable for the electrodes of a clique to be placed equidistant one another to facilitate enhanced electrogram fidelity.

Aspects of the present disclosure are directed toward various hi-density electrode array catheters with substantially uniform electrode spacing and/or known and constant spacing between electrodes. The array of electrodes includes a plurality of bi-pole pairs that facilitate electrophysiology mapping of tissue in contact with the electrodes. More advanced embodiments of the present disclosure may utilize orientation independent sensing/omnipolar technology ("OIS/OT") and related algorithms to mitigate the need for substantially square electrode arrays. OIS/OT and related algorithms are discussed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, all of which are hereby incorporated by referenced as though fully disclosed herein.

Conventional mapping catheter designs employ bi-pole electrode configurations to detect, measure, and display electrical signals from the heart. However, such conventional mapping catheter designs may be prone to error associated with the orientation of the bi-pole electrode pairs relative to an electrical wavefront of the heart, and result in sensed electrical signals and electrophysiology mapping results that may be orientation dependent; and accordingly may not actually reflect the tissue properties. To mitigate this risk, aspects of the present disclosure are directed to signal processing techniques which may sample a plurality of bi-pole electrode pair configurations, with varying orientations, to produce electrophysiology mapping results which are independent of orientation. To facilitate such signal processing techniques, respective electrophysiology mapping catheters (e.g., linear, planar array, and basket) may utilize cliques of electrodes with spacing that is constant over time.

Various embodiments of the present disclosure are directed to electrophysiology mapping catheters, such as linear arrays and basket catheters, where each spline and/or arm includes more than one column of electrodes extending a length of the catheter—negating the need to take measurements across splines/arms. This greatly improves the accuracy of the resulting electrical signal maps, as the relative distance of electrodes on the same arm/spline are not prone to changes in distance over time as electrodes on adjacent arms/splines. Moreover, the electrophysiology basket catheters, during a diagnostic procedure, may be operated anywhere between an expanded and contracted state as the relative distance between electrodes within a clique on each arm/spline does not change during movement of the catheter arms/splines, or in response to tissue contact.

Further aspects of the present disclosure are directed toward eliminating a distal cap of an electrophysiology basket catheter, which facilitates the sampling of electrogram data from the distal most tip of the basket.

Details of the various embodiments of the present disclosure are described below with specific reference to the figures.

FIG. 1A is a plan view of a tip portion 110 of a planar array catheter 101 for high-density electrophysiology mapping, consistent with various embodiments of the present disclosure. The tip portion 110 includes a flexible array of (micro)electrodes $102_{1-N}$ distributed along a top surface of arms 103, 104, 105, 106. The four longitudinally-extending arms comprise the flexible framework of the planar array. In various embodiments of the present disclosure, the arms 103, 104, 105, 106 are flexible printed circuit boards. In the present embodiment, each arm includes two columns of electrodes $102_{1-N}$ extending a length of the arms. The relative spacing of the electrodes, in some embodiments, may be between 1.5-3 millimeters (center-to-center spacing). While various embodiments of the present disclosure are directed to spot electrodes that are printed on flexible circuit boards, such embodiments may be readily adapted to facilitate the use of ring electrodes on the arms 103, 104, 105, 106 with the position and spacing disclosed herein. The four arms 103, 104, 105, 106 comprise a first outboard arm 103, a second outboard arm 106, a first inboard arm 104, and a second inboard arm 105. These arms may be laterally separated from each other (when deployed) by approximately 3.3 millimeters ("mm"), for example. In some specific embodiments, the relative spacing of the electrodes $102_{1-N}$ may be 1 mm or less. Although the planar array depicted herein includes four arms 103, 104, 105, 106, other embodiments with varying numbers of arms, relative electrode spacing, the number of total electrodes on each arm, the number of rows and columns of electrodes on each arm, and placement of electrodes on one or both sides of the planar array are readily adaptable and envisioned by the present disclosure.

Consistent with the embodiment disclosed in FIG. 1A, some specific embodiments of the planar array catheter may include electrodes of varying sizes. For example, the most-distal electrode 102 on the first outboard arm 103 and/or the most-proximal electrode 102 on the second outboard arm 106 may be larger in surface area. These enlarged electrodes may be used, for example, for precise localization of the flexible array in impedance-based navigation systems. In some embodiments, the larger electrodes may facilitate tissue ablation. In such an embodiment, the larger electrodes may be driven with an ablation current between two or more of the larger electrodes, if desired, for bipolar ablation, or, alternatively to drive ablation current in a unipolar mode between one or both of the enlarged electrodes and, for example, a patch electrode located on a patient (e.g., on the patient's back). Unipolar or bipolar ablation may also be conducted between the smaller electrodes and/or a combination of smaller and larger electrodes 102. Alternatively or concurrently, current may travel between one or more of the enlarged electrodes and any one or all of the smaller electrodes. This unipolar or bipolar ablation may be used to create specific lines or patterns of lesions.

As further shown in FIG. 1A, a catheter shaft 107 is coupled to a tip portion 110 (including the planar array) via a proximal bushing 108 which receives the one or more arms 103, 104, 105, 106 of the planar array. A distal portion of the catheter shaft 107 may include radiopaque marker bands 111 to facilitate fluoroscopic visualization of the catheter within a patient's cardiovascular system. In other embodiments, the radiopaque marker bands 111 may be localization coils to facilitate visualization of the planar array in an impedance-based, magnetic-based, or hybrid type navigation system (e.g., such as the MediGuide™ System sold by Abbott Laboratories). In further embodiments, the planar array may include a combination of radiopaque marker bands and localization coils.

Figure 1C:
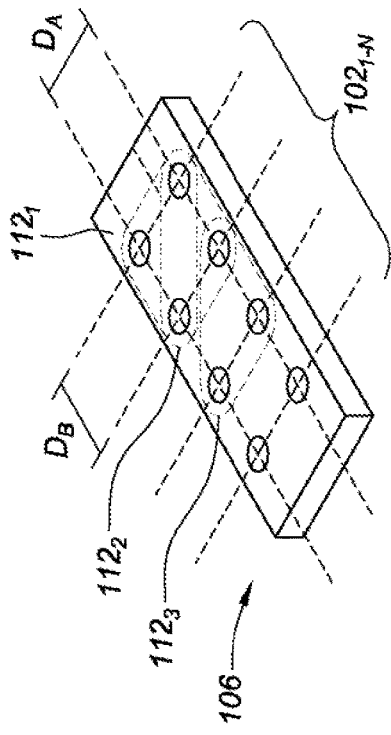
FIG. 1C is a close-up, isometric view of an arm portion of the planar array catheter of FIG. 1A, consistent with various embodiments of the present disclosure.
Figures 1B, 1D:
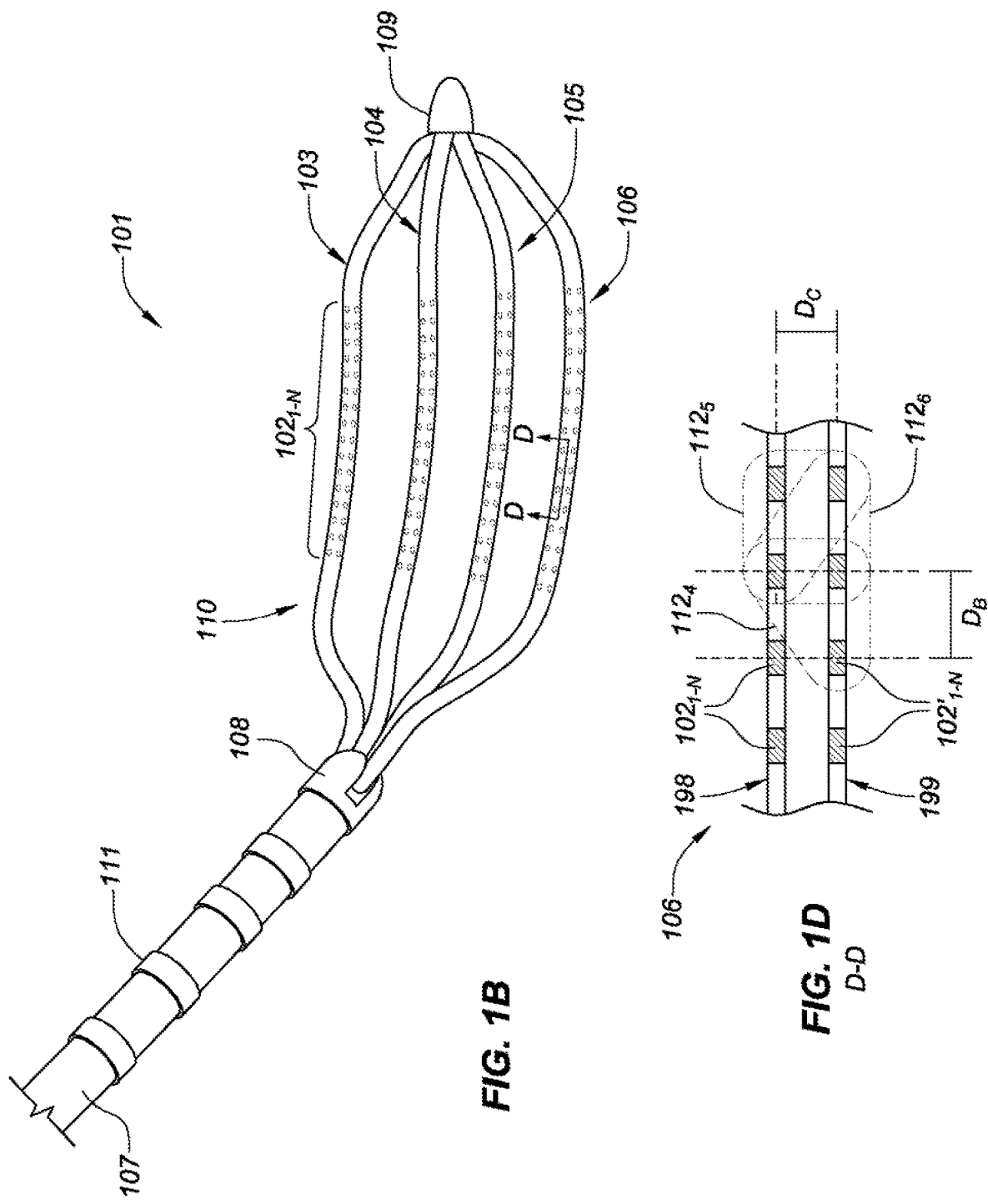
FIG. 1B is an isometric side view of the tip portion of the planar array catheter of FIG. 1A depicted in a flexed configuration, consistent with various embodiments of the present disclosure.
FIG. 1D is a cross-sectional, side view of the planar array catheter of FIG. 1A, consistent with various embodiments of the present disclosure.

FIG. 1B is an isometric side view of the tip portion 110 of the planar array catheter 101 of FIG. 1A for high-density electrophysiology mapping and is depicted in a flexed configuration (representing contact between the catheter tip and cardiac tissue), consistent with various embodiments of the present disclosure. In FIG. 1B, the planar, flexible arms 103, 104, 105, 106 are flexed to conform to the cardiac tissue (not shown), enabling a physician to maintain contact between several of the electrodes $102_{1-N}$ and the tissue. This enhances the accuracy, and the corresponding diagnostic value, of the recorded information concerning the heart's electrical activity.

While many embodiments of the present disclosure are directed to electrophysiology mapping, embodiments of the present disclosure may also be configured for pacing (as well). For example, one or more electrodes $102_{1-N}$ may send pacing signals to, for example, cardiac tissue.

While some embodiments are directed to a planar array structure substantially comprising flexible printed circuits, the arms 103, 104, 105, 106 may alternatively (or in addition to) include (or be reinforced with) a flexible or spring-like material such as nitinol. The construction (including, for example, the length and/or diameter of the arms) and material composition of the arms may be tailored for specific applications. For example, desired resiliency, flexibility, foldability, conformability, and stiffness characteristics (including one or more characteristics that may vary from the proximal end of a single arm to the distal end of that arm, or between or among the plurality of arms comprising the planar array). The foldability of materials such as nitinol, or flexible circuit board materials (e.g., thin polymer films) provides the additional advantage of facilitating insertion of the planar array into a delivery catheter or introducer, whether during delivery of the catheter into the body or removal of the catheter from the body at the end of a procedure.

The high-density electrode configuration of the various electrophysiology mapping catheters disclosed herein may find particular application for (1) defining regional propagation maps on, for example, one millimeter square areas within the atrial walls of the heart; (2) identify complex fractionated atrial electrograms for ablation; (3) identify localized, focal potentials between the electrodes for higher electrogram resolution; and/or (4) more precisely target areas for ablation. The mapping catheters and ablation catheters disclosed herein are constructed to conform to, and remain in contact with, cardiac tissue despite (potentially erratic) cardiac motion. The contact stability of the catheters disclosed herein during cardiac motion facilitates improved mapping accuracy and ablation contiguity due to sustained tissue-electrode contact. While various embodiments of the present disclosure are presented in terms of endocardial applications, the catheters described herein may also be directed for use in epicardial applications.

Though not shown in FIGS. 1A-B, various embodiments of the planar array catheter 101 may include one or more irrigation ports. For example, a proximal irrigant port(s) may be located on/at the distal end of proximal bushing 108, the proximal irrigant port(s) positioned to deliver irrigant to or near the point where the electrode carrying arms 103, 104, 105, 106 exit from the distal end of the proximal bushing 108 that is mounted on the distal end of the catheter shaft 107 in this embodiment. In some more specific embodiments, a second, distal irrigation port(s) may be located near the distal intersection of the arms 103, 104, 105, 106 and on or near distal tip 109. In yet further embodiments, if desired, multiple irrigation ports could be present at various positions along the arms 103-106. Where more than one irrigant port is positioned at proximal and/or distal ends of the planar array 110, more uniform irrigant distribution at or near the proximal/distal apex of the arms 103-106 may be facilitated.

FIG. 1C is a close-up, isometric view of a portion of arm 106 of the high-density mapping catheter 101 of FIG. 1A, consistent with various embodiments of the present disclosure. The arm 106 includes two columns of electrodes $102_{1-N}$ extending along a length of the arm. Each set of three adjacent electrodes forms a clique of electrodes $112_{1-3}$. Each clique is capable of mapping the electrophysiology of tissue in contact therewith in a manner that is independent of the orientation of an individual bi-pole electrode pair within the clique used to sense the electrical characteristics of the tissue. Specifically, the cliques are capable of sampling the electrical signal passing through the contact tissue in at least two orientations. For example, a first bi-pole pair of electrodes in an example clique $112_1$ samples an electrical signal passing through the contact tissue in an x-orientation, and a second bi-pole pair of electrodes in the clique $112_1$ samples a second electrical signal passing through the contact tissue in a y-orientation. Signal processing circuitry may then be used to determine the true electrical signal for that location. The two bi-pole pairs, though substantially in the same location and in contact with the same tissue volume, may sample different electrical characteristics of the tissue due to the directionality of the electrical activation wave fronts traveling through the heart. The electrical activation wave fronts typically emanate from a sinoatrial node, and atrio-ventricular node; however, interfering electrical signals may also emanate from one or more of the pulmonary veins.

Importantly, to facilitate determination of important electrical characteristics of the tissue (e.g., impedance), the distance between the first bi-pole pair ($D_A$) and the distance between the second bi-pole pair ($D_B$) must be known and/or constant. In FIGS. 1A-D, the spacing of electrodes $102_{1-N}$ on arms 103-106 is constant. Furthermore, in various embodiments it may be desirable for the distance between the two sets of bi-pole pairs for a single clique 112 to be the same ($D_A$=$D_B$).

FIG. 1D is a cross-sectional, side view of an arm 106 of the planar array catheter 101 of FIG. 1A, consistent with various embodiments of the present disclosure. As shown in FIG. 1D, some embodiments of the planar array catheter 101 may include a complimentary set of electrodes to the two columns of electrodes $102_{1-N}$ mounted on a top surface 198 of the arm 106. The second set of electrodes $102'_{1-N}$ facilitates both electrophysiology mapping with either side of the planar array, as well as the ability to detect electrical signal flow through the cardiac muscle in a z-orientation. As discussed in reference to FIG. 1C, a set of electrode cliques $112_{1-3}$ on a top surface 198 of the planar array may detect electrical signal flow through the cardiac tissue in x and y orientations, while another electrode 102' on the bottom surface 199 of the planar array (when used in conjunction with one of the electrodes 102 of the same clique on the top surface 198) facilitates determination of electrical characteristics in the z-orientation. FIG. 1D shows a number of cliques $112_{4-6}$ from a cross-sectional, side view of the planar array catheter 101. Similar to the positioning of the electrodes 102 on the top surface 198, it is desirable for the distance between the bottom electrodes 102' ($D_B$), and the depth of the circuit board (Dc) to be known. Furthermore, in various embodiments it is desirable for the distance between the two sets of bi-pole pairs for a single clique 112' to be the same ($D_B$=Dc).

Figure 2A:
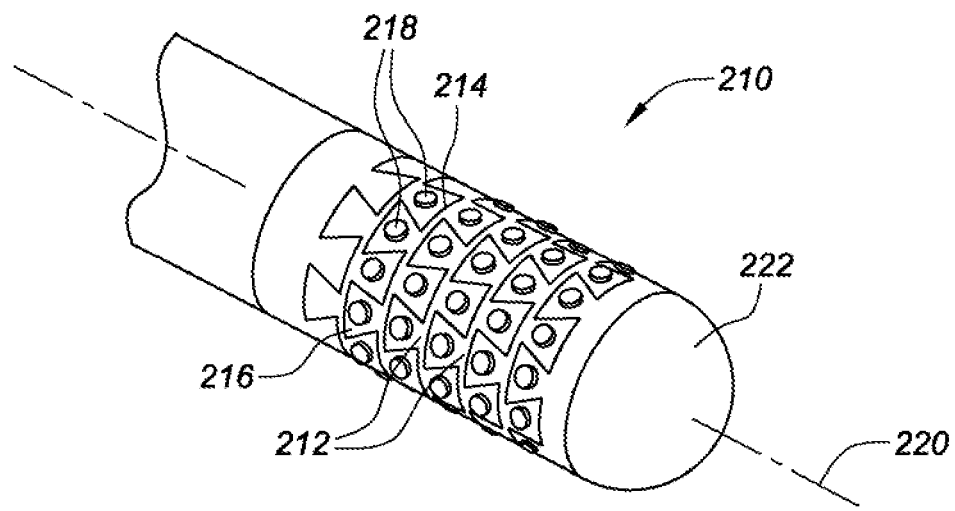
FIG. 2A is a partial, isometric view of a high-density mapping catheter, consistent with various embodiments of the present disclosure.

FIG. 2A is a partial, isometric view of a linear, high-density mapping catheter assembly portion 210, consistent with various embodiments of the present disclosure. As shown in FIG. 2A, the tip portion 210 includes interlocking rings or bands 212 of non-conductive material (e.g., polyether-etherketone also referred to as PEEK) forming the underlying support framework for a plurality of electrodes 218. In this embodiment, a circumferential or helical through-cut pattern 214 defines a plurality of dovetail surfaces 216. Each dovetail surface 216 has an electrode 218 attached to it, thereby defining a flexible array of electrodes that are arranged in circumferential rings or bands about the tip portion 210 of the linear mapping catheter. The electrodes 218 are also aligned in longitudinally-extending (e.g., parallel to a catheter longitudinal axis 220) rows of electrodes that are able to flex or move slightly relative to each other during use of the catheter (e.g., contact with tissue). The non-conductive material of the bands 212 individually insulates each electrode 218 from one another. The non-conductive substrate on which the electrodes 218 are mounted may comprise PEEK. In some embodiments, the tip 210 may include a radiopaque tip cap 222 that facilitates fluoroscopic visualization. The tip cap may be dome shaped, hemispherical, flat-topped, tapered, or any other desired general shape.

Figure 2B:
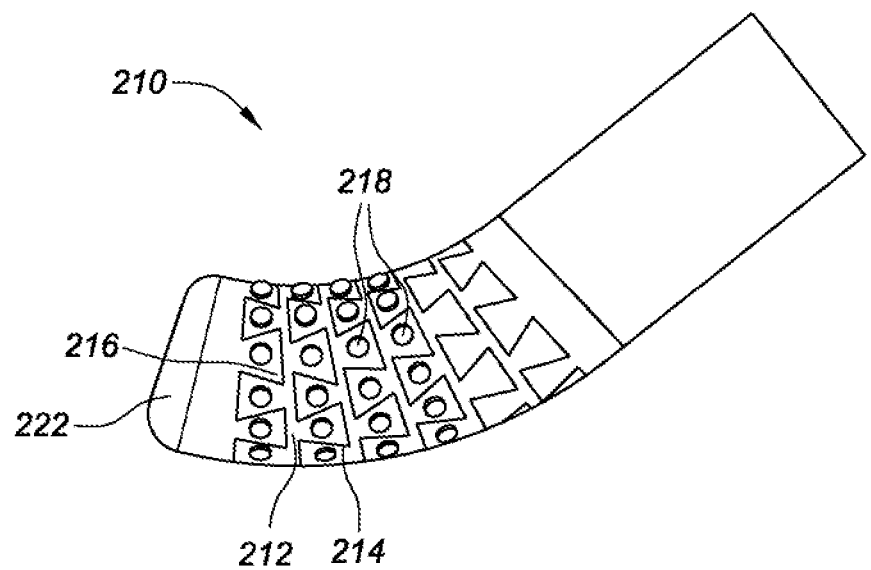
FIG. 2B is a partial, isometric view of the high-density mapping catheter shown in FIG. 2A depicted in a flexed configuration, representing contact between the catheter tip and cardiac tissue, consistent with various embodiments of the present disclosure.
Figure 2C:
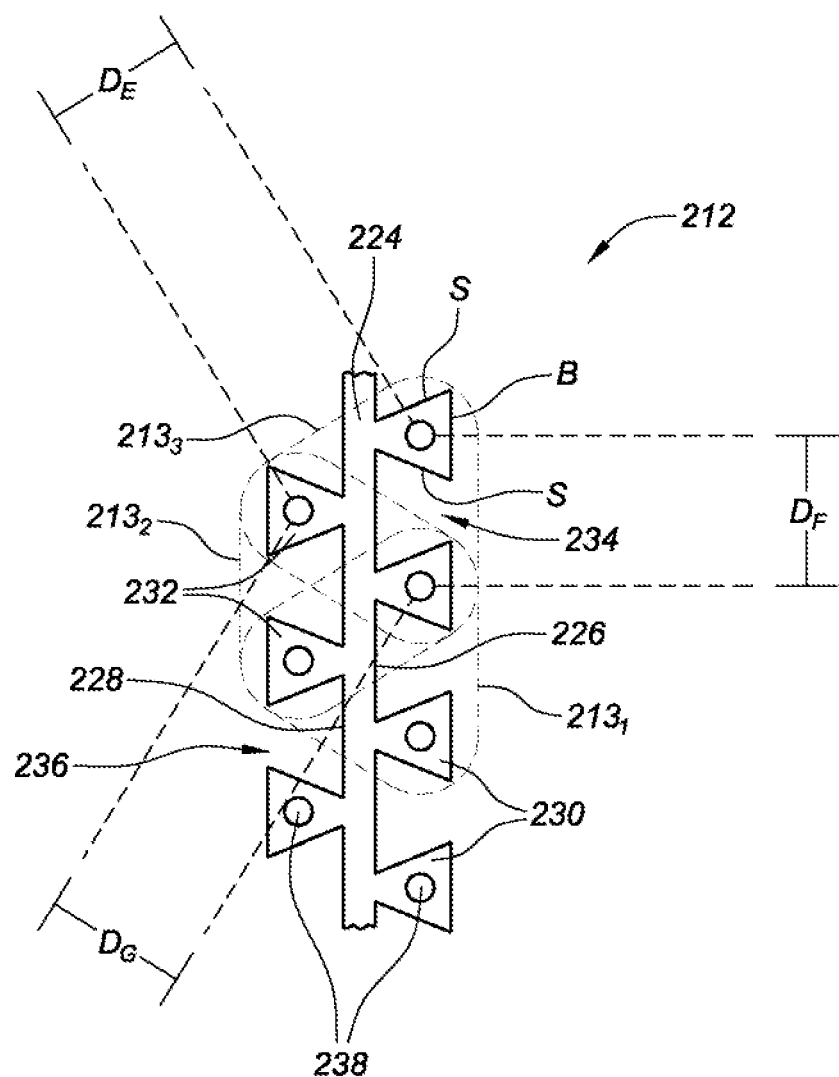
FIG. 2C is a partial view of a flat pattern design of an electrode carrier band on the high-density mapping catheter shown in FIG. 2A, consistent with various embodiments of the present disclosure.

In the embodiment of the tip portion 210 shown in FIG. 2A-C, there are approximately sixty-four discrete electrodes 218, and either separate lead wires that extend to each of the electrodes 218 from the proximal end of the catheter or one or more flexible circuit boards within the tip portion 210 that are electrically/communicatively coupled to each of the electrodes 218 and signal processing circuitry (located near a proximal end of the catheter). In some embodiments, the catheter may be either 7 French or 7.5 French in diameter. The flexible tip 210 helps to facilitate sustained electrode contact with cardiac tissue during, for example, cardiac motion, which in turn improves the accuracy of the resulting cardiac electrical activity map. The circumferential or helical cuts 214, which may be formed by a laser, create a plurality of serpentine gaps that permit the tip to flex as the cardiac wall moves in a beating heart. When a plurality of circumferential through-cuts are used, a plurality of dovetailed (or 'saw-toothed') bands 212 are formed.

As in the previous embodiments, each of the electrodes 218 are positioned equidistant relative to one another, or at least at known or constant distances relative to one another.

FIG. 2B is a partial, isometric view of the high-density mapping catheter assembly portion 210 shown in FIG. 2A, depicted in a flexed configuration. The flexed configuration representing contact between the catheter tip 210 and cardiac tissue. While in contact with tissue, the resulting flex of the flexible tip 210 along the helical cuts 214 between each of the dovetailed bands 212 creates minute changes in the relative positions of the electrodes 218. As the total flexure of the tip 210 is divided across a plurality of electrode bi-pole pairs, the total effect on the resulting cardiac electrical activity map is greatly mitigated.

The linear, high-density mapping catheter of FIGS. 2A-B may include an irrigated configuration. In the irrigated configuration, the catheter may include irrigant ports that extend through the dovetailed bands 212 and/or irrigant may be excreted through the helical cuts 214 (serpentine gaps) between interleaving pairs of the dovetailed bands 212.

FIG. 2C is a partial view of a flat pattern design of an electrode carrier band (also referred to as a dovetailed band) 212 on the high-density mapping catheter shown in FIG. 2A, consistent with various embodiments of the present disclosure.

As shown in FIG. 2C, the pattern includes a circumferential waistline or ring 224 defined between a circumferentially-extending proximal edge 226 and a circumferentially-extending distal edge 228. Each of these edges is interrupted by a plurality of proximally-extending pads 230 or distally-extending pads 232. Each pad in this embodiment has the shape of a truncated isosceles triangle with sides S and a base B. Two adjacent proximally-extending pads define a proximally-opening pocket 234 between them. Similarly, on the opposite side of the circumferential waistline 224, two distally-extending pads 232 that are adjacent to each other define a distally-opening pocket 236.

When two dovetail bands 212 are connected, each distally-extending pad 232 flexibly interlocks in a proximally-opening dovetailed pocket 234 (of the adjacent dovetail band 212), and each proximally-extending pad 230 flexibly interlocks in a distally-opening dovetail pocket 236 (of another adjacent dovetail band 212). The interlocking pads 230 and 232, and pockets 234 and 236, of each band 212 define a plurality of serpentine gaps between alternating electrode-carrier bands 212 which facilitate deformation of the catheter tip 210 in response to a force exerted on the tip. In the present embodiment, each of the pads 230, 232 includes an aperture 238 in which an electrode will be mounted. Each aperture 238 may extend through the respective pad, from a pad outer surface to a pad inner surface.

In other embodiments, instead of circumferential through-cuts 214 (see, e.g., FIGS. 2A-B), which define a plurality of individual electrode-carrier bands 212, the flexible tip may be formed by a continuous helical cut.

While the embodiments of FIGS. 2A-C show bands 212 with longitudinally offset pads 230 and 232 on either side of waistline 224, other embodiments may include a carrier band with a plurality of bowtie-shaped or hourglass-shaped structures extending across the waistline 224 (instead of the offset pads 230 and 232). Each of the bowtie-shaped or hourglass-shaped structures having electrode-mounting apertures 238 on one or more sides of the waistline 224. Such embodiments are essentially symmetrical about the waistline 224, except where electrode-mounting apertures are placed only on one side of the bowtie-shaped or hourglass-shaped structures.

As shown in FIG. 2C, each band 212 includes two columns of electrodes, with each electrode coupled to a respective electrode-mounting aperture 238. The two columns of electrodes extending along a waistline 224 of the band 212, with the relative placement of the electrodes in each column longitudinally offset relative to one another. The resulting formation creates a plurality of triangular cliques of electrodes $213_{1-3}$ formed from three adjacent electrodes. Each clique 213 is capable of mapping the electrophysiology of tissue in contact therewith, in a manner that is independent of the orientation of a single bi-pole electrode pair. Specifically, the triangular cliques 213 of the present embodiment are capable of sampling the electrical signal passing through the contact tissue in three directions (offset from one another by approximately 60°). Signal processing circuitry may then be used to determine the true electrical signal characteristics for that location, regardless of bi-pole pair sampling orientation. Importantly, to facilitate determination of important electrical characteristics of the tissue (e.g., impedance), the distance between the first bi-pole pair ($D_E$), second bi-pole pair ($D_F$), and third bi-pole pair ($D_G$) must be known and constant. In FIG. 2C, the spacing of the electrodes on the band 212 are not only known and constant, but the spacing between each of the electrodes in the clique 213 are equal. Accordingly, the distance between each of the three sets of bi-pole pairs for the clique $213_1$ are equal ($D_E=D_F=D_G$).

The relative spacing of the electrode mounting apertures 238 in FIG. 2C (and thereby the electrodes), in some embodiments, may be between 1.5-3 millimeters (center-to-center spacing). In some specific embodiments, the relative spacing of the electrode mounting apertures 238 may be 1 mm or less.

Figure 3A:
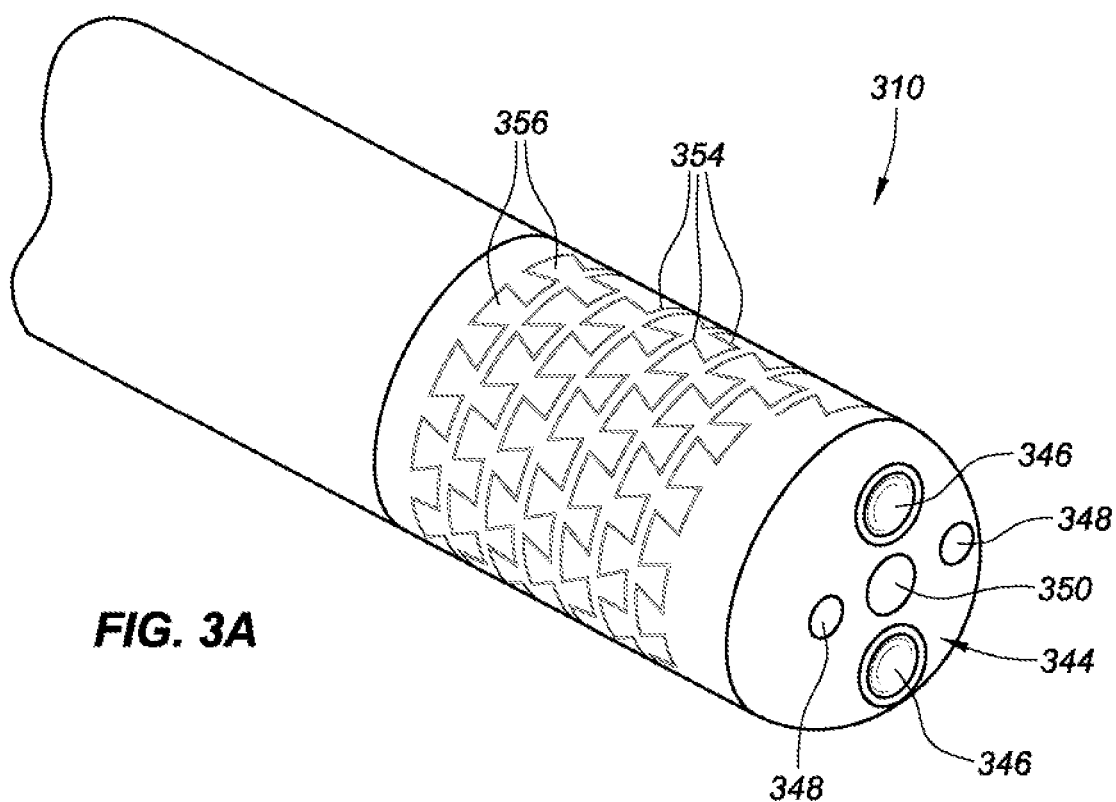
FIG. 3A is a partial, isometric view of a tip region of an ablation catheter having distal high-density mapping electrodes, consistent with various embodiments of the present disclosure.
Figure 3B:
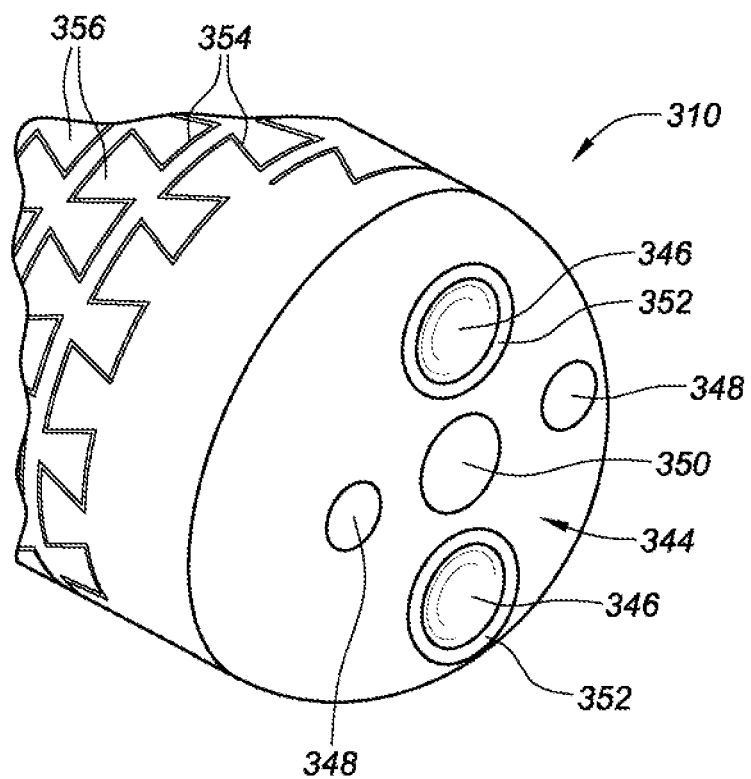
FIG. 3B is an enlarged, partial view of the distal tip of the ablation catheter of FIG. 3A, consistent with various embodiments of the present disclosure.

FIG. 3A is a partial, isometric view of a tip portion 310 of an ablation catheter having distal high-density mapping electrodes and FIG. 3B is an enlarged, partial view of the distal tip of the ablation catheter of FIG. 3A, consistent with various embodiments of the present disclosure.

As shown in FIGS. 3A-B an ablation catheter tip portion 310 is depicted with an interlocking, dovetailed pattern 356 formed from conductive material to facilitate tissue ablation of contacted tissue via thermal/electrical energy transfer. Each of the dovetailed patterns 356 that extend circumferentially about the tip portion 310 are separated by a serpentine cut 354. The distal end 344 of this flexible ablation tip 310 includes a pair of symmetrically-placed, high-density microelectrodes 346 for electrophysiology mapping. The distal end further includes two front-facing irrigation ports 348, and a thermocouple or temperature sensor 350. The mapping electrodes 346 may be mounted in a nonconductive insert 352 (as shown in FIG. 3B) to electrically insulate the mapping electrodes from the remainder of the ablation tip. In such a configuration, the flexible ablation tip 310 may be approximately 4-8 millimeters long. In the embodiment of FIGS. 3A-B, the pads and pockets of the interlocking, dovetailed pattern 356 defined by the serpentine cuts 354 may be smaller than the corresponding pads and pockets depicted in, for example, FIGS. 2A-C, the individual pads of the tip portion 310 do not house electrodes. Though in other embodiments, the pads and pockets of FIGS. 2A-C may be combined with the distal end 344 of FIG. 3A—facilitating two arrays of high-density electrodes on a single catheter.

In some embodiments of the ablation catheter tip portion 310 of FIGS. 3A-B, the irrigant ports 348 may be replaced with additional mapping electrodes 346. The resulting square pattern of the mapping electrodes 346 facilitates the use of the electrodes in bi-pole pair arrangements. With three or more mapping electrodes, forming a clique, on the distal end 344 of the tip portion 310, the resulting bi-pole pair arrangements may be independently addressable to facilitate determination of electrical characteristics in both x and y directions. To further facilitate measuring electrical characteristics in a z-direction, one or more mapping electrodes may be placed on a shaft of the ablation catheter (at approximately the same center-to-center spacing as the other mapping electrodes in the clique). Signal processing circuitry receiving the electrical signals from the electrodes may then be used to determine the true electrical signal for that location, independent of the orientation of the bi-pole pairs. In such embodiments, the distal end 344 may still include irrigant ports.

In some embodiments where a z-direction measurement is desirable, four or more electrodes may be used to form a "pyramid shaped" clique of electrodes.

Some specific embodiments, in accordance with the present disclosure, may combine the embodiments of FIGS. 2A-C, and 3A-B with a combination of mapping electrodes on a distal end 344 circumferentially and longitudinally extending along a tip portion 210/310 of the catheter shaft. The resulting embodiment facilitates electrophysiology mapping of tissue in contact with a distal end 344 of the catheter tip portion 310 (as in FIGS. 3A-B) and/or a distal tip portion of the catheter shaft. This allows the clinician during a electrophysiology diagnostic procedure to make contact with target tissue in various relative orientations (e.g., perpendicular, parallel, etc.).

Figure 4A:
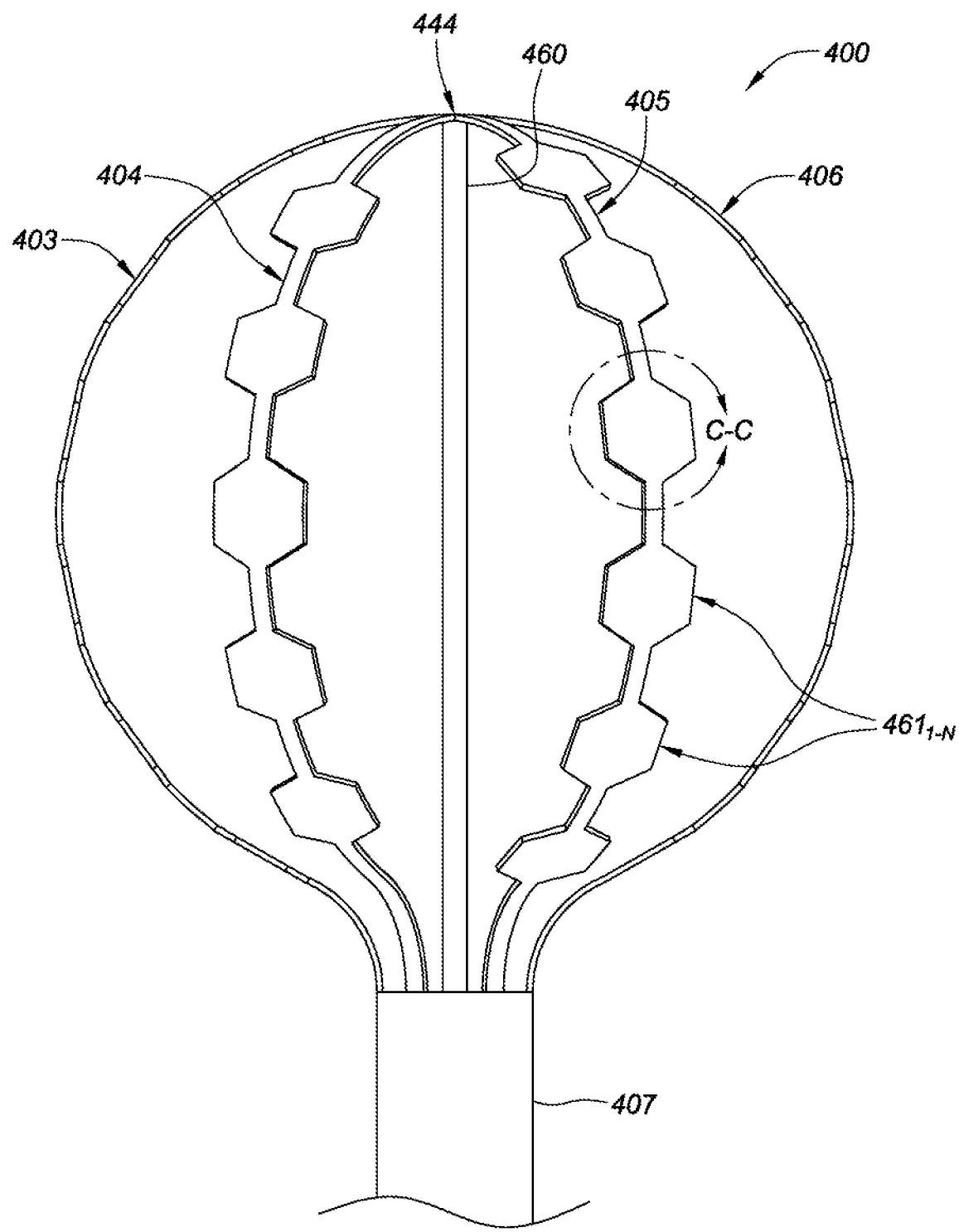
FIG. 4A is a plan view of a basket catheter in an expanded configuration, consistent with various embodiments of the present disclosure.

FIG. 4A is a plan view of a distal portion of a basket catheter 400 in an expanded configuration, consistent with various embodiments of the present disclosure. The basket is comprised of a plurality of splines 403, 404, 405, 406 which are coupled to a catheter shaft 407 at a proximal end and to a distal cap or one another at a distal end 444. While the present embodiment presents a basket comprised of four splines 403, 404, 405, 406, basket catheters with three or more splines are readily envisioned with the design depending on an intended clinical application and desired electrophysiology mapping granularity. To facilitate expansion/contraction of the basket, a deployment member 460 extends along a longitudinal axis of the basket. The deployment member in some embodiments may be a pull-wire, which extends proximally to a catheter handle at a proximal end of the catheter shaft 407. Actuation of the pull-wire causes expansion/contraction of the basket. In other embodiments, the deployment member 460 may be a lumen which may be actuated by a manipulator on the catheter handle to expand/contract the basket.

Figures 4B, 4C:
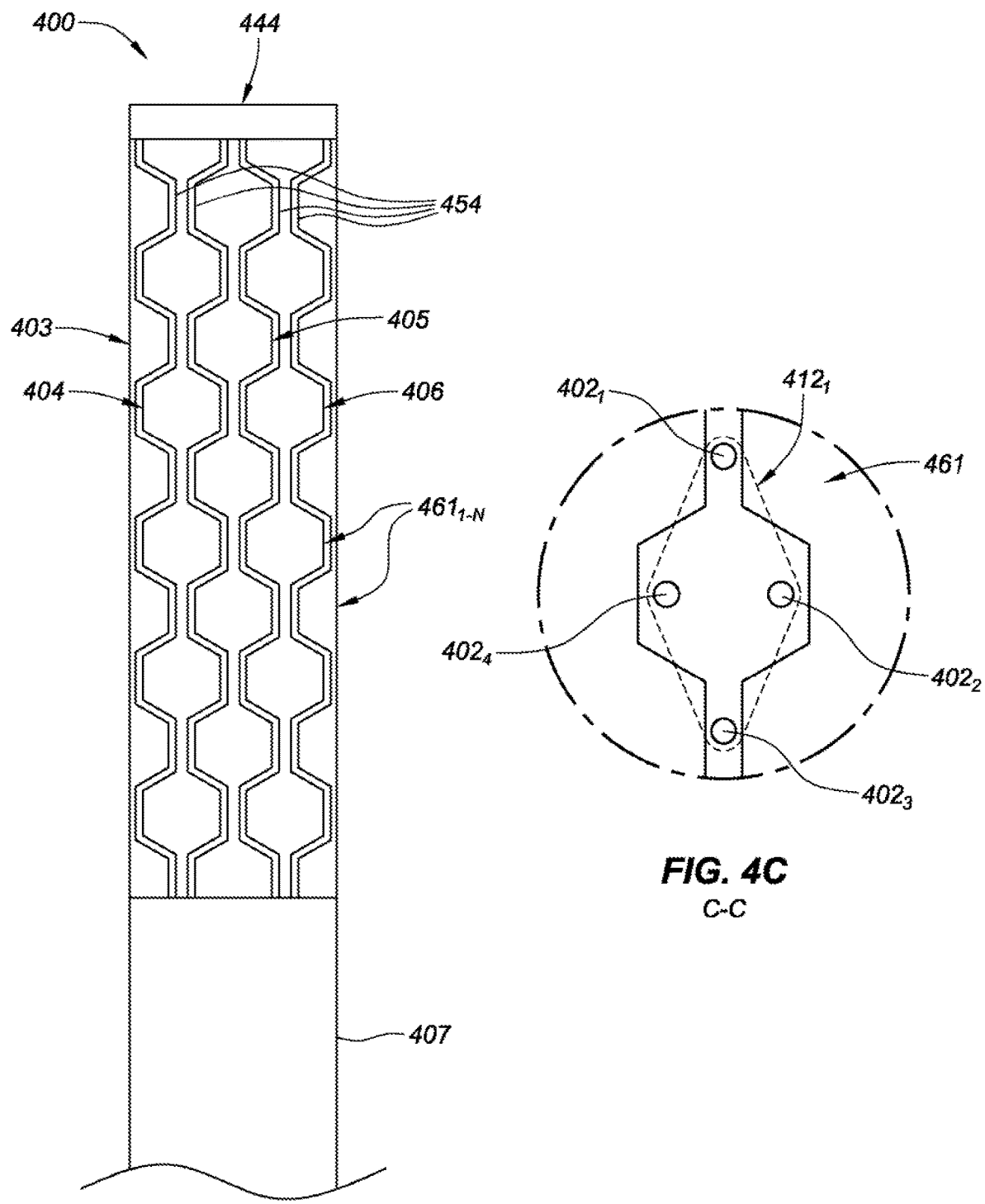
FIG. 4B is a plan view of the basket catheter of FIG. 4A in a contracted configuration, consistent with various embodiments of the present disclosure.
FIG. 4C is an enlarged, plan view of a spline section of the basket catheter of FIG. 4A, consistent with various embodiments of the present disclosure.

In the present embodiment, each of the splines 403, 404, 405, 406 includes electrode islands $461_{1-N}$ distributed along a length of each spline. While the embodiments presented in FIGS. 4A-C depict electrode islands $461_{1-N}$ regularly distributed along the length of each spline, other embodiments may include electrode islands $461_{1-N}$ unevenly distributed along the splines. For example, in pulmonary vein electrophysiology mapping applications, only a distal portion of the basket may be in contact with tissue proximal the pulmonary veins. Accordingly, a distribution of electrode islands $461_{1-N}$ may be weighted toward a distal end 444 of the basket to facilitate enhanced electrophysiology mapping granularity in proximity to the pulmonary veins.

Various embodiments of the present disclosure are directed to electrode islands $461_{1-N}$ on each of the respective splines 403, 404, 405, 406, with the electrode islands $461_{1-N}$ on adjacent splines being longitudinally offset to facilitate interleaving when the basket is being delivered via an introducer sheath in a contracted configuration.

FIG. 4B is a plan view of a distal portion of the basket catheter 400 of FIG. 4A in a contracted configuration, consistent with various embodiments of the present disclosure. Small serpentine gaps 454 are located between each of the adjacent splines 403, 404, 405, 406. In the contracted configuration of the basket catheter, a deployment member 460 (as shown in FIG. 4A) may be extended distally to allow each of the splines to be drawn in radially to a longitudinal axis of the catheter shaft 407. In various embodiments of the present disclosure, the splines 403, 404, 405, 406 may have a natural set in either an expanded/contracted state, and utilize the deployment member 460 to overcome the natural set.

As shown in FIG. 4B, electrode islands $461_{1-N}$ on adjacent splines 403, 404, 405, 406 are longitudinally offset to facilitate interleaving (also referred to as interlocking or nesting) the electrode island minimizing collapsed basket catheter package size. To facilitate the collapsed state of the splines 403, 404, 405, 406, the relative distance between catheter shaft 407 and distal end 444 is increased via deployment member 460.

FIG. 4C is an enlarged, plan view of a portion of spline 405 of FIG. 4A. The enlarged, plan view further shows one of the plurality of electrode islands $461_{1-N}$ distributed along a length of the spline 405. The electrode islands $461_{1-N}$ may include three or more electrodes 402 configured in a clique $412_1$. The cliques of electrodes may be used in various bi-pole configurations to facilitate measurement of electrical characteristics of tissue in contact with the electrodes. Each clique is capable of measuring signals indicative of the unique orientation specific electrical characteristics of the tissue in at least two or more orientations. For example, clique $412_1$ in the present embodiment includes four electrodes $402_{1-4}$. A first bi-pole pair includes electrodes $402_{1,3}$ facilitating the collection of tissue electrical characteristic data in an orientation substantially parallel with the catheter's longitudinal axis. A second bi-pole pair includes electrodes $402_{2,4}$ facilitating the collection of tissue electrical characteristic data in an orientation substantially transverse to the catheter's longitudinal axis. To facilitate collecting this electrical data, these bi-pole electrode pairs may be independently addressable by signal processing circuitry. The signal processing circuitry analyzes the received signals from the electrodes in the clique to determine orientation independent electrophysiology information of the tissue in contact with the clique electrodes.

While the present embodiment depicts each of the electrodes $402_{1-4}$ in the clique $412_1$ positioned on an exterior surface of the spline 405, to further detect contact tissue electrical characteristics in a third direction, or z-direction (e.g., normal to tissue), a fifth electrode in the clique may be mounted to an interior surface of the spline 405. The fifth electrode may be a non-contact electrode, and may be paired with at least one of the electrodes $402_{1-4}$ on the exterior surface of the spline 405 to determine the electrical characteristics of the tissue in the z direction.

In various embodiments consistent with the present disclosure, the splines and electrode islands may be formed from flexible electronic circuit boards with each of the electrodes coupled thereto and communicatively coupled to signal processing circuitry via electrical traces that extend along interior or exterior surfaces of the flexible printed circuit board. In some specific embodiments, each of the splines may consist of a nitinol strut. The flex circuit may be either bonded directly to the nitinol, or, alternatively, the flex circuit may be directly bonded to pebax tubing which houses the nitinol strut internally.

In some specific embodiments, the electrodes may be 0.8 millimeters in diameter with a total surface area of 0.5 mm². The electrodes in each clique may be various sizes and shapes. For example, a smaller size electrode(s) (e.g., 0.8 mm in diameter) for electrophysiology mapping, and larger size electrode(s) that may be capable of both electrophysiology mapping and have a large enough impedance to facilitate localization in an impedance or hybrid-based catheter navigation system (e.g., MediGuide™ System, and/or EnSite NavX system). In one particular embodiment, the smaller electrophysiology mapping catheters may be coupled to an external-facing surface of the splines for direct contact with tissue, with larger, non-contact navigation electrodes coupled to an internal-facing surface of the splines.

While it may be desirable in some embodiments to have equal spacing between all of the electrodes in a clique, knowledge of the relative spacing between each of the electrodes which form bi-pole pairs is sufficient to accurately capture orientation-specific electrical characteristic data of tissue in contact with the electrodes. In some specific embodiments, edge-to-edge spacing for one or more of the bi-pole pairs of electrodes may be between 2-2.5 millimeters. To simplify signal processing, consistent spacing between all of the electrodes in a clique or across the entire basket catheter may be desirable. In yet other specific embodiments, center-to-center spacing of the electrodes in a clique may be between 0.5-4 millimeters.

Various embodiments of the present disclosure are directed to cliques of electrodes forming a 2×2 array, and a triangular-shaped clique with electrodes positioned at each corner. Any of these clique configurations are sufficient to determine contacted tissue electrical characteristics in two or more orientations. Some embodiments of the triangular-shaped clique may form a right-triangle or an isosceles triangle. Some embodiments of the isosceles triangle include a vertex angle between 30-140°. More complex cliques may include five or more electrodes to facilitate sampling electrical characteristics of a tissue at relative orientations of less than 90°. Such an embodiment further reduces the electrophysiology mapping error associated with the directionality of an electrical wavefront traveling through the heart.

Figure 5A:
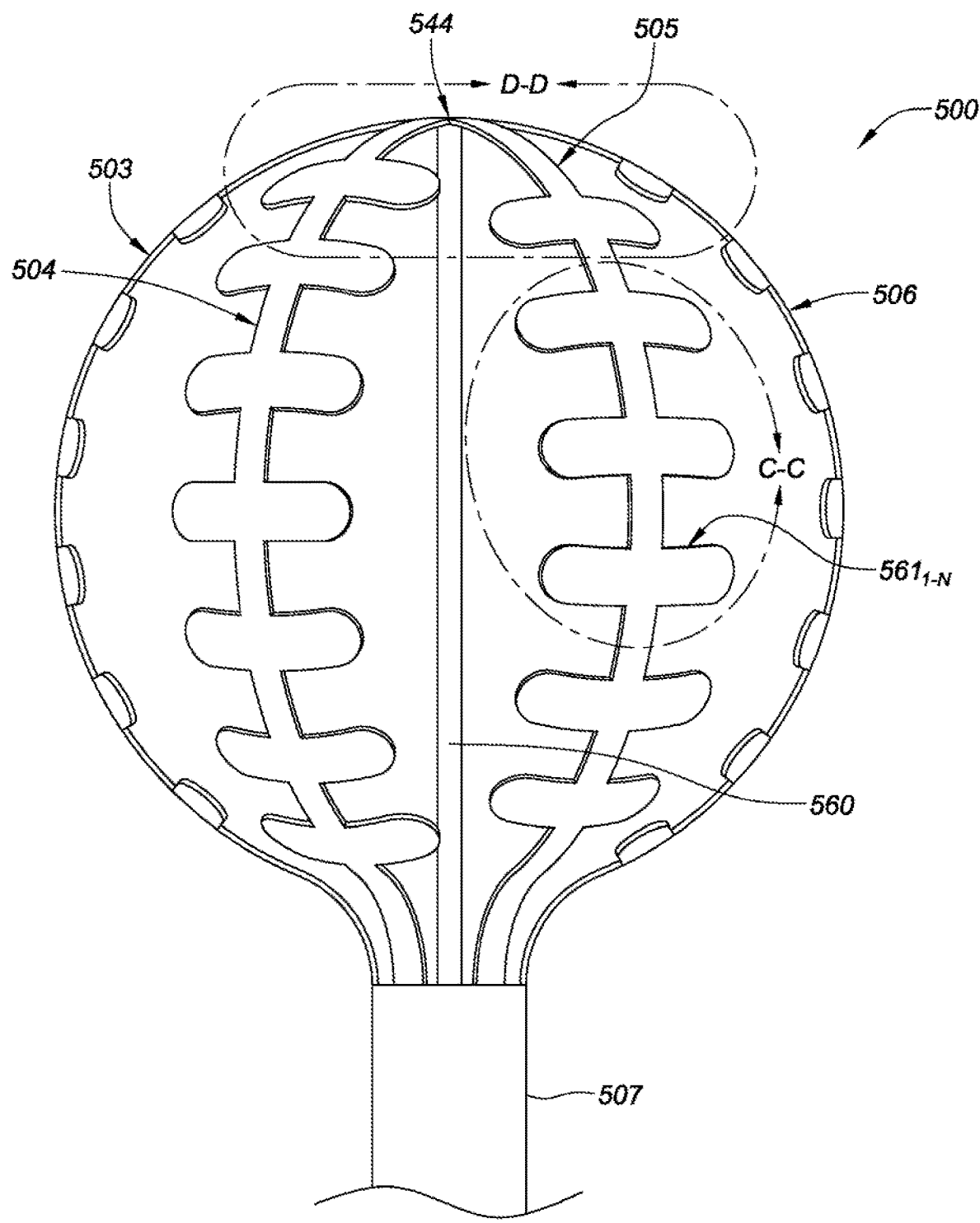
FIG. 5A is a plan view of a basket catheter in an expanded configuration, consistent with various embodiments of the present disclosure.

FIG. 5A is a plan view of a basket catheter 500 in an expanded configuration, consistent with various embodiments of the present disclosure. The basket is comprised of a plurality of splines 503, 504, 505, 506 which are coupled to a catheter shaft 507 at a proximal end and to a distal cap or one another at a distal end 544. While the present embodiment presents a basket comprised of four splines 503, 504, 505, 506, basket catheters with three or more splines are readily envisioned with the design depending on an intended clinical application and desired electrophysiology mapping granularity. To facilitate expansion/contraction of the basket, a deployment member 560 extends along a longitudinal axis of the basket. The deployment member in some embodiments may be a pull-wire, which extends proximally to a catheter handle at a proximal end of the catheter shaft 507. Actuation of the pull-wire causes expansion/contraction of the basket.

In the present embodiment, each of the splines 503, 504, 505, 506 includes ribs $561_{1-N}$ distributed about a length of each spline. Each of the ribs extends transverse to a direction of the mating spline. The splines and ribs facilitate distribution of electrodes across inner and/or outer surfaces thereof. In various embodiments, the splines and ribs are formed from flexible electronic circuit boards, and/or have flexible electronic circuit boards adhered to one or more surfaces of the splines and ribs. Each of the electrodes may be communicatively and mechanically coupled to the flexible circuit board via pads, with electrical traces communicatively coupling the electrodes to signal processing circuitry.

While the embodiment presented in FIGS. 5A-D depicts ribs $561_{1-N}$ regularly distributed along the length of each spline 503, 504, 505, 506, other embodiments may include ribs $561_{1-N}$ unevenly distributed along the splines. For example, in pulmonary vein electrophysiology mapping applications, only a distal portion of the basket may be in contract with tissue proximal the pulmonary veins. Accordingly, a distribution of ribs $561_{1-N}$ may be weighted toward a distal end 544 of the basket to facilitate enhanced electrophysiology mapping granularity in proximity to the pulmonary veins.

Various embodiments of the present disclosure are directed to ribs $561_{1-N}$ on each of the respective splines 503, 504, 505, 506, with the ribs $561_{1-N}$ on adjacent splines being longitudinally offset to facilitate interleaving when the basket is being delivered via an introducer sheath in a contracted configuration.

Figure 5B:
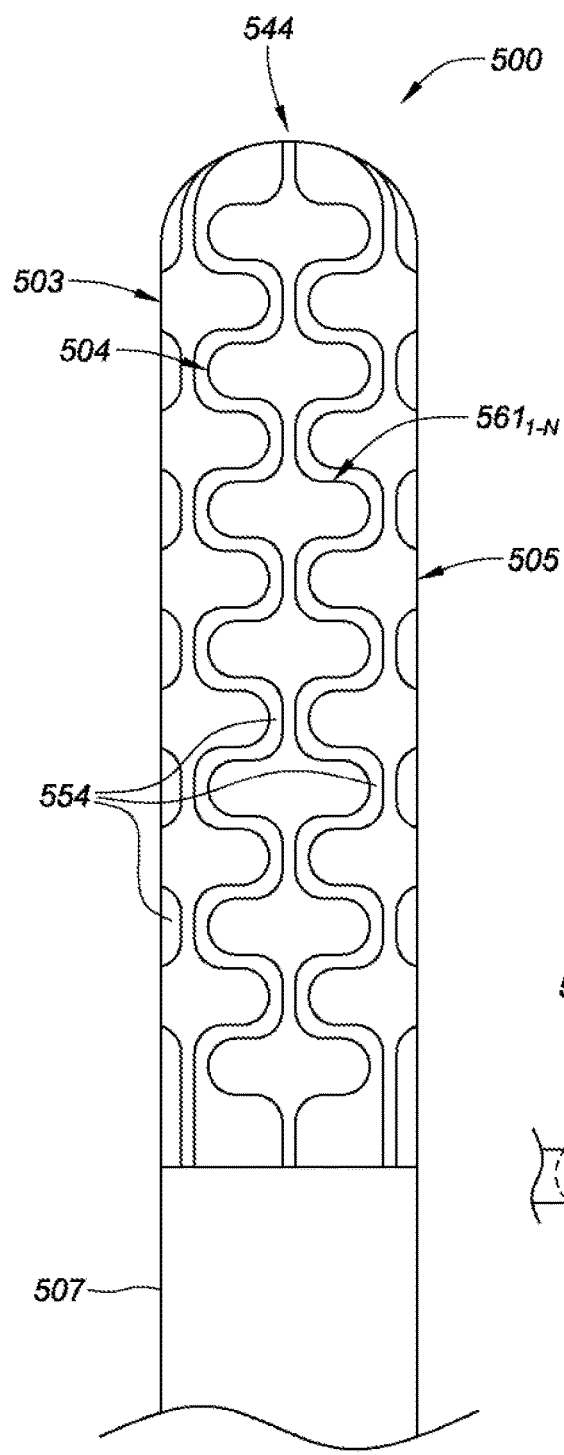
FIG. 5B is a plan view of the basket catheter of FIG. 5A in a contracted configuration, consistent with various embodiments of the present disclosure.

FIG. 5B is a plan view of the basket catheter 500 of FIG. 5A in a contracted configuration, consistent with various embodiments of the present disclosure. Small serpentine gaps 554 are located between each of the adjacent splines 503-506. In the contracted configuration of the basket catheter, a deployment member 560 (as shown in FIG. 5A) may be extended distally to allow each of the splines to be drawn in radially toward a longitudinal axis of the catheter shaft 507.

As shown in FIG. 5B, ribs $561_{1-N}$ on adjacent splines 503-506 are longitudinally offset to facilitate interleaving the ribs to minimize collapsed basket catheter package size. To facilitate the collapsed state of the splines 503-506, the relative distance between catheter shaft 507 and distal end 544 is increased via deployment member 560.

Figure 5C:
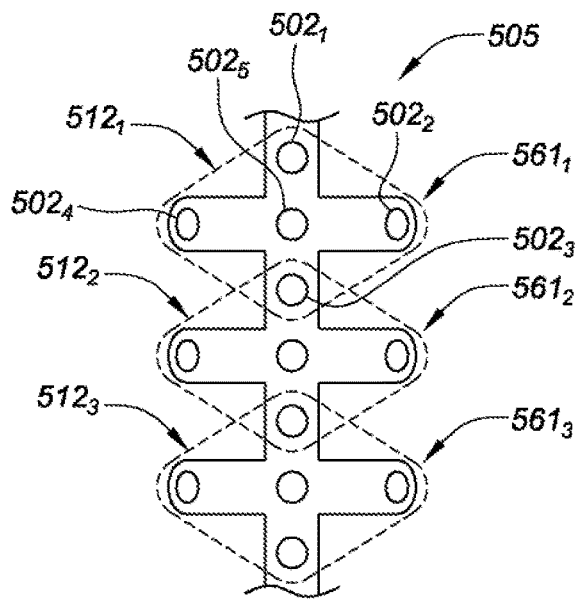
FIG. 5C is an enlarged, plan view of a spline section of the basket catheter of FIG. 5A, consistent with various embodiments of the present disclosure.

FIG. 5C is an enlarged, plan view of a portion of spline 505 of FIG. 5A, consistent with various embodiments of the present disclosure. The enlarged, plan view further showing three of the ribs $561_{1-3}$ distributed along a length of the spline 505. The spline 505 and ribs $561_{1-3}$ may house a plurality of electrodes for electrophysiology mapping of cardiovascular tissue, for example. As shown in FIG. 5C, the plurality of electrodes 502 are configured in three overlapping cliques $512_{1-3}$. Each clique of electrodes may be used in various bi-pole configurations to facilitate measurement of electrical characteristics of tissue in contact with the electrodes. Each clique is capable of measuring the directionally distinct electrical characteristics of the contacted tissue in two or more orientations. For example, clique $512_1$ in the present embodiment includes five electrodes $502_{1-5}$. A first bi-pole pair may include, for example electrodes $502_{1,3}$ facilitating the collection of tissue electrical characteristic data in an orientation substantially parallel with the catheter's longitudinal axis. A second bi-pole pair includes electrodes $502_{2,4}$ facilitating the collection of tissue electrical characteristic data in an orientation substantially transverse to the catheter's longitudinal axis.

In some specific embodiments, some of the electrodes 502 within a clique 512 may be multi-purpose, while other electrodes are single-purpose. For example, electrodes $502_{1,3}$ may function as both navigation and electrophysiology mapping electrodes, electrodes $502_{2,4}$ may function only as electrophysiology mapping electrodes, and electrode $502_5$ may function only as a navigation electrode. In various embodiments of the present disclosure, the cliques form a two-dimensional shape (e.g., triangle, square, hexagon, etc.).

While the present embodiment depicts each of the electrodes $502_{1-5}$ in the clique $512_1$ positioned on an exterior surface of the spline 505, to further detect tissue electrical characteristics in a third orientation (i.e., normal to tissue), one or more electrodes in the clique may be mounted to an interior surface of the spline 505. The fifth electrode may be a non-contact electrode, and be paired with at least one of the electrodes $502_{1-5}$ on the exterior surface of the spline 505 to determine the electrical characteristics of the contacted tissue in a normal direction relative to a surface of the tissue. Moreover, as the navigation electrodes do not necessarily need to be in contact with tissue, the navigation-only electrodes may be placed on the interior surface of the spline 505.

Figure 5D:
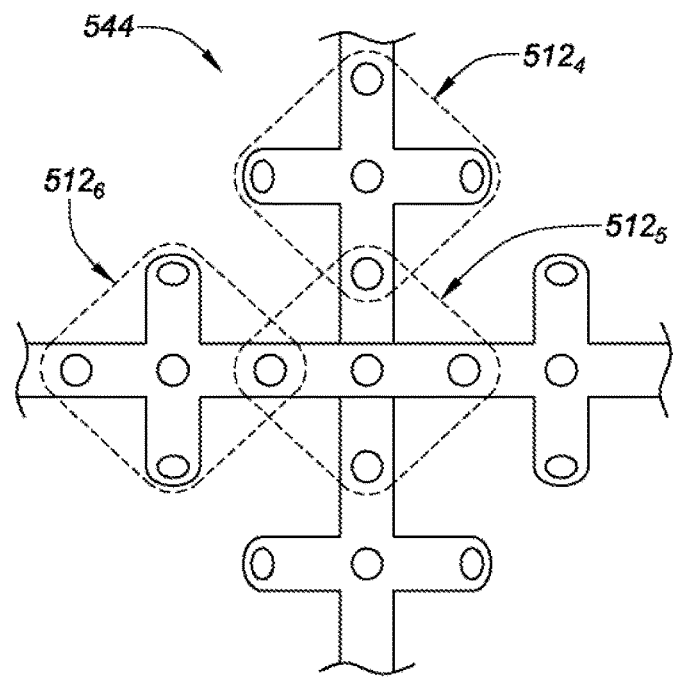
FIG. 5D is an enlarged, top view of the basket catheter of FIG. 5A, consistent with various embodiments of the present disclosure.

FIG. 5D is an enlarged, top view of a distal end 544 of the basket catheter of FIG. 5A, consistent with various embodiments of the present disclosure. FIG. 5D further shows the placement of electrode cliques $512_{4-6}$ in proximity to the distal end 544 of the basket catheter. This distal placement of electrodes may be particularly advantageous in various applications (e.g., electrophysiology mapping of left atrium with specific focus on the electrical signals emanating in and around the pulmonary vein).

Figure 6A:
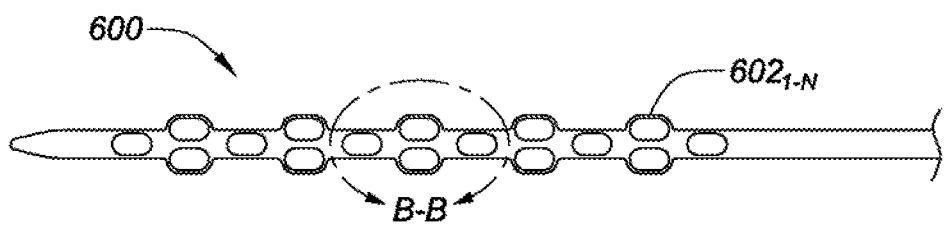
FIG. 6A is a plan view of a basket catheter spline, consistent with various embodiments of the present disclosure.
Figure 6B:
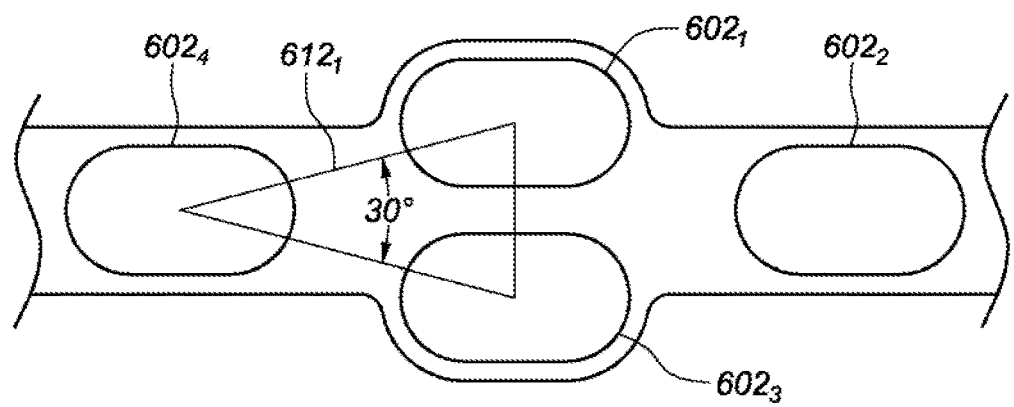
FIG. 6B is an enlarged, plan view of a portion of the basket catheter spline of FIG. 6A, consistent with various embodiments of the present disclosure.

FIG. 6A is a plan view of a basket catheter spline 600 and FIG. 6B is an enlarged, plan view of a portion of the basket catheter spline 600 of FIG. 6A, consistent with various embodiments of the present disclosure. The basket catheter spline 600 includes a plurality of electrodes $602_{1-N}$ which may be associated with one or more cliques 612. As shown in FIG. 6B, electrodes $602_{1,3-4}$ are configured in an electrode clique $612_1$. The electrodes in the clique $612_1$ may be independently addressable by signal processing circuitry to detect electrical characteristics of tissue in contact with the electrodes via one or more electrode bi-pole pairs in the clique which allow for the detection of electrical signal variation associated with the directional flow of electrical signals through a cardiac muscle, for example. In the present embodiment, the electrode clique forms an isosceles triangles with a vertex angle of approximately 30°.

As shown in FIG. 6B, a number of the electrodes, electrodes $602_{1,3}$ for example, are not positioned along a centerline of the spline 600. Instead, the electrodes $602_{1,3}$ are positioned offset from the centerline of the spline 600 on pads to form the desired triangular clique $612_1$ arrangement. In such an embodiment, an adjacent spline may have its electrodes longitudinally offset to facilitate interleaving of the respective pads extruding from each spline when contracting the basket catheter.

Figure 7A:
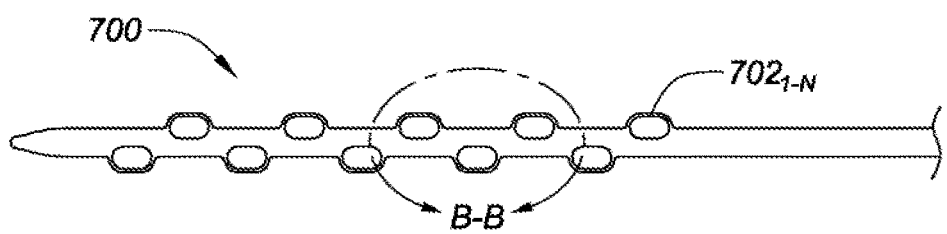
FIG. 7A is a plan view of a basket catheter spline, consistent with various embodiments of the present disclosure.
Figure 7B:
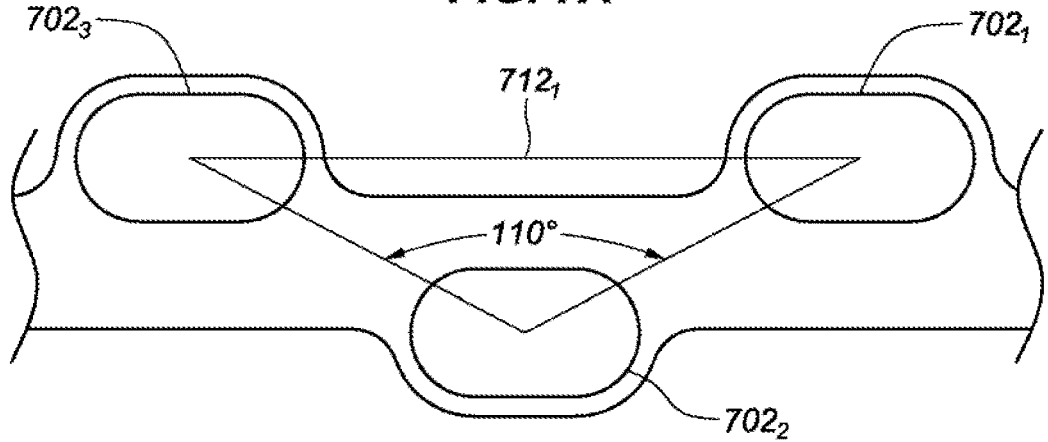
FIG. 7B is an enlarged, plan view of a portion of the basket catheter spline of FIG. 7A, consistent with various embodiments of the present disclosure.

FIG. 7A is a plan view of a basket catheter spline 700 and FIG. 7B is an enlarged, plan view of a portion of the basket catheter spline 700 of FIG. 7A, consistent with various embodiments of the present disclosure. The basket catheter spline 700 includes a plurality of electrodes $702_{1-N}$ which may be associated with one or more cliques 712. As shown in FIG. 7B, electrodes $702_{1-3}$ are configured in an electrode clique $712_1$. In the present embodiment, the electrode clique forms an isosceles triangle with a vertex angle of approximately 110°.

As shown in FIG. 7B, each of the electrodes 702 are positioned offset from the centerline of the spline 700 on pads to form the triangular clique 712 arrangement. In such an embodiment, an adjacent spline on the basket catheter may have its electrodes longitudinally offset to facilitate interleaving of the respective pads extruding from each spline when contracting the basket catheter.

Figures 8A, 8B:
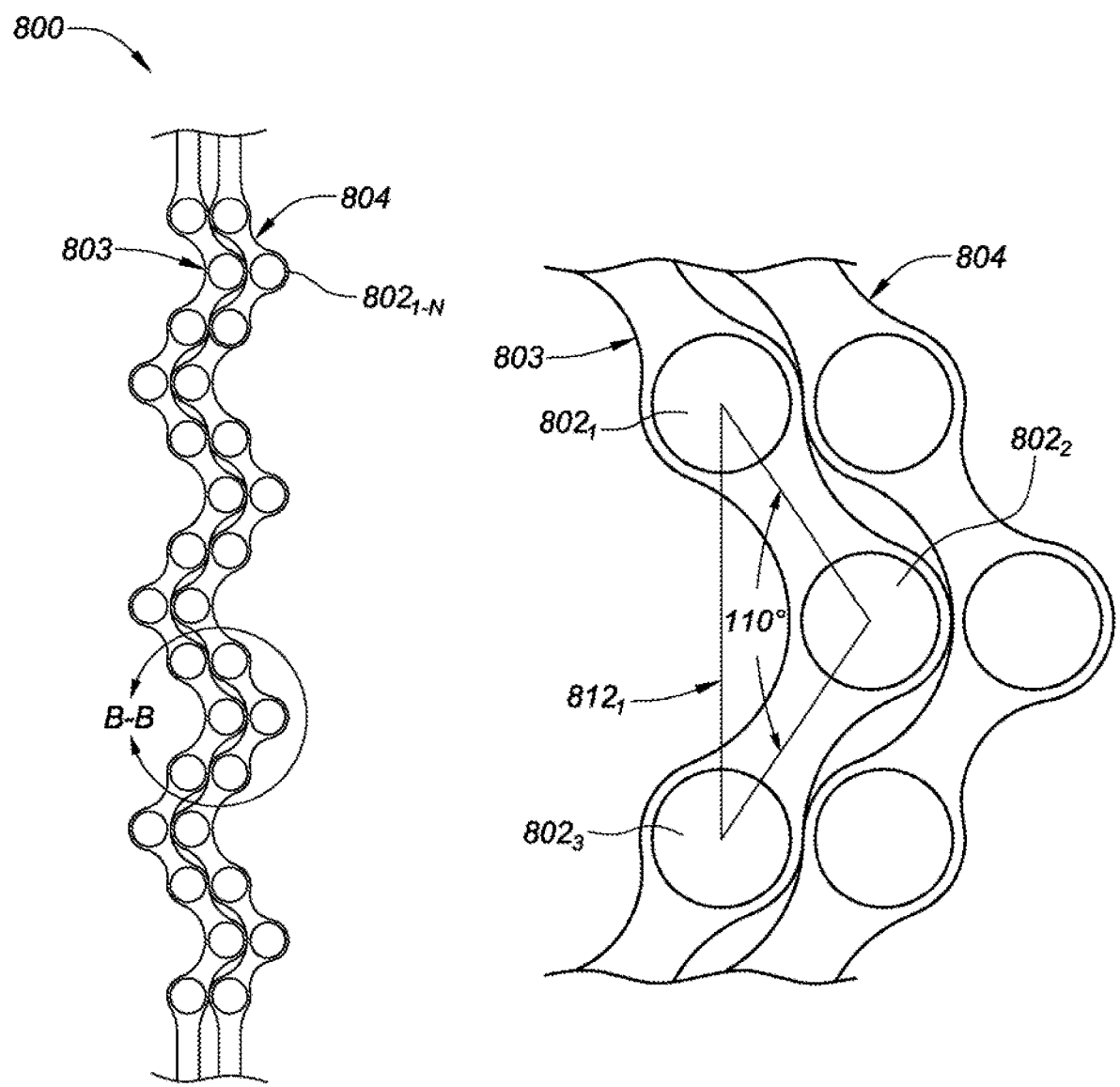
FIG. 8A is a plan view of two interleaved basket catheter splines, consistent with various embodiments of the present disclosure.
FIG. 8B is an enlarged, plan view of a portion of the two interleaved basket catheter splines of FIG. 8A, consistent with various embodiments of the present disclosure.

FIG. 8A is a plan view of two interleaved basket catheter splines 800 and FIG. 8B is an enlarged, plan view of a portion of the two interleaved basket catheter splines 800 of FIG. 8A, consistent with various embodiments of the present disclosure. The two splines 803 and 804 include a plurality of electrodes $802_{1-N}$ distributed along a length of the splines. In the present embodiment, each of the splines 803 and 804 have a "saw-tooth" shape that facilitates seating adjacent splines into complimentary features thereof when the basket catheter is contracted. The saw-tooth shape further facilitates triangular cliques $812_1$ of electrodes $802_{1-3}$, which in some embodiments form an isosceles triangle with a vertex angle of approximately 110°.

In some embodiments consistent with the present disclosure, the cliques of electrodes remain in a triangular-shape even when the basket catheter is in a collapsed configuration. In various embodiments, the triangular-shaped cliques of electrodes are formed from immediately adjacent electrodes.

While various embodiments of high-density electrode catheters are disclosed herein, the teachings of the present disclosure may be readily applied to various other catheter embodiments as disclosed, for example, in the following patents and patent applications which are hereby incorporated by reference: U.S. provisional application No. 61/753,429, filed 16 Jan. 2013; U.S. provisional application No. 60/939,799, filed 23 May 2007; U.S. application Ser. No. 11/853,759 filed 11 Sep. 2007, now U.S. Pat. No. 8,187,267, issued 29 May 2012; U.S. provisional application No. 60/947,791, filed 3 Jul. 2007; U.S. application Ser. No. 12/167,736, filed 3 Jul. 2008, now U.S. Pat. No. 8,206,404, issued 26 Jun. 2012; U.S. application Ser. No. 12/667,338, filed 20 Jan. 2011 (371 date), published as U.S. patent application publication no. US 2011/0118582 A1; U.S. application Ser. No. 12/651,074, filed 31 Dec. 2009, published as U.S. patent application publication no. US 2010/0152731 A1; U.S. application Ser. No. 12/436,977, filed 7 May 2009, published as U.S. patent application publication no. US 2010/0286684 A1; U.S. application Ser. No. 12/723,110, filed 12 Mar. 2010, published as U.S. patent application publication no. US 2010/0174177 A1; U.S. provisional application No. 61/355,242, filed 16 Jun. 2010; U.S. application Ser. No. 12/982,715, filed 30 Dec. 2010, published as U.S. patent application publication no. US 2011/0288392 A1; U.S. application Ser. No. 13/159,446, filed 14 Jun. 2011, published as U.S. patent application publication no. US 2011/0313417 A1; international application no. PCT/US2011/040629, filed 16 Jun. 2011, published as international publication no. WO 2011/159861 A2; U.S. application Ser. No. 13/162,392, filed 16 Jun. 2011, published as U.S. patent application publication no. US 2012/0010490 A1; U.S. application Ser. No. 13/704,619, filed 16 Dec. 2012, which is a national phase of international patent application no. PCT/US2011/040781, filed 16 Jun. 2011, published as international publication no. WO 2011/159955 A1.

While the various embodiments presented in FIGS. 1-8 are amenable to the application of spot electrodes coupled to a flexible electronic circuit, where the flexible electronic circuit may also (partially) comprise the splines, arms, and shaft of the various catheters, yet other embodiments may be directed to the use of ring electrodes crimped or swagged onto splines, arms, and shafts comprising well-known materials in the art. The ring electrodes being electrically coupled to signal processing circuitry using lead wires. The ring electrodes being positioned along the splines, arms, and shafts of the catheters to form cliques of electrodes with equal and known spacing therebetween. In yet other embodiments, ring electrodes may be swagged or crimped onto a flexible circuit board comprising at least part of the splines, arms, and/or shaft of the various catheters disclosed herein.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A planar array catheter comprising:
   an elongated catheter shaft including a proximal end and a distal end, and defining a catheter longitudinal axis extending between the proximal and distal ends; and
   a flexible, planar array at the distal end of the catheter shaft, the planar array configured to conform to tissue, and includes two or more arms extending substantially parallel with the longitudinal axis, each of the arms having a plurality of electrodes mounted thereon; and
   wherein the electrodes on each arm are grouped into cliques of three or more electrodes on each arm.

2. The planar array catheter of claim 1, wherein the plurality of electrodes on each arm are configured in at least two columns oriented substantially parallel with the catheter longitudinal axis.

3. The planar array catheter of claim 1, wherein the cliques of electrodes are configured in a triangular-shape, each clique having at least three electrodes, the cliques of electrodes configured to sample electrical characteristics of contacted tissue in at least two substantially transverse directions.

4. The planar array catheter of claim 3, wherein the electrical characteristics sampled by the electrodes in a clique are collectively indicative of the true electrical characteristics of the tissue independent of an orientation of the planar array relative to the tissue.

5. The planar array catheter of claim 1, wherein each of the two or more arms of the planar array includes electrodes on both an inner and outer surface, each of the cliques include at least one electrode on an inner surface of the arm, the at least one electrode on the inner surface of the arm configured to facilitate sampling of electrical characteristics in a direction normal to the contacted tissue.

6. The planar array catheter of claim 1, wherein a distance between at least two pairs of electrodes within each clique is equal.

7. The planar array catheter of claim 1, wherein a distance between the electrodes in each clique remains constant in contracted and deployed configurations of the planar array.

8. The planar array catheter of claim 1, wherein a center-to-center distance between the electrodes in each clique is between 0.5 and 4 millimeters.

9. The planar array catheter of claim 1, wherein the electrodes of the cliques form an isosceles triangle with a vertex angle between 30°-140°.

10. The planar array catheter of claim 1, wherein the electrodes of the cliques form a right triangle.

11. The planar array catheter of claim 1, wherein the plurality of electrodes are spot electrodes and the two or more arms include flexible electronic circuits that are communicatively and mechanically coupled to the spot electrodes.

12. The planar array catheter of claim 1, wherein the electrodes of a clique are configured to collect electrical signals emanating from the tissue in contact with the planar array indicative of the electrical characteristics of the tissue, the electrical characteristics of the tissue being independent of an orientation of the planar array relative to the tissue.

\* \* \* \* \*